(12) United States Patent
Knight (10) Patent No.: US 9,687,379 B1
(45) Date of Patent: Jun. 27, 2017

(54) CERVICAL RESTRAINT PADDING SYSTEM

(71) Applicant: Tamera L Knight, Santa Rosa, CA (US)

(72) Inventor: Tamera L Knight, Santa Rosa, CA (US)

( * ) Notice: Subject to any disclaimer, the term of this patent is extended or adjusted under 35 U.S.C. 154(b) by 471 days.

(21) Appl. No.: 14/021,805

(22) Filed: Sep. 9, 2013

Related U.S. Application Data (60) Provisional application No. 61/699,386, filed on Sep. 11, 2012.

(51) Int. Cl.
*A61F 5/055* (2006.01)

(52) U.S. Cl.
CPC .................... *A61F 5/055* (2013.01)

(58) Field of Classification Search
CPC .............. A61F 5/012; A61F 2007/0008; A61F 2007/0009; A61F 2007/0018; A61F 2007/0042; A61F 2007/0056; A61F 2007/0238; A61F 7/00; A61F 7/03; A61F 7/08; A61F 7/10; A61F 7/106; A61F 5/01; A61F 5/055; A61F 5/05891; A61F 5/05883; A61F 5/028; A61F 5/024; A61F 5/026; A61F 13/12; A61F 13/128; A42B 3/0473; A47C 7/383
USPC ................. 602/17, 18; 128/DIG. 23
See application file for complete search history.

(56) References Cited

U.S. PATENT DOCUMENTS

| | | | | |
|---|---|---|---|---|
| 3,810,466 A | * | 5/1974 | Rogers | 602/18 |
| 4,538,597 A | * | 9/1985 | Lerman | 602/18 |
| 4,759,089 A | * | 7/1988 | Fox | 5/636 |
| 6,468,239 B1 | * | 10/2002 | Mollura, Sr. | A61F 5/0111 128/882 |
| 6,494,854 B1 | * | 12/2002 | Visness et al. | 602/18 |
| 6,848,136 B2 | * | 2/2005 | Sonobe | A47G 9/10 5/655.9 |
| 6,926,686 B2 | * | 8/2005 | Cheatham | 602/18 |

* cited by examiner

*Primary Examiner* — Ophelia A Hawthorne
(74) *Attorney, Agent, or Firm* — Edward S. Sherman (57) ABSTRACT

A neck restraint system for surgical candidates and recovering patients has at least one or more rigid or semi-rigid members including a fabric cover for supporting a plurality of cushioning or padding elements. The cushions elements are preferably conformable fabric bags partially filled with either memory elastic foam and/or foam beads to provide conformability. The fabric cover provides for exterior cosmetic customization and secure juxtaposition of replaceable and/or exchangeable cushioning elements. The cushioning elements are disposed over and around the edges portions of the rigid or semi-rigid restraint members that would otherwise rub, chafe or abrade the skin even if padded. Periodic changes of the type of cushioning elements prevent and alleviate such skin irritation and provide greater patient comfort.

21 Claims, 7 Drawing Sheets

FIG. 1A

PRIOR ART

PRIOR ART

CERVICAL RESTRAINT PADDING SYSTEM

CROSS REFERENCE TO RELATED APPLICATIONS

The present application claims the benefit of priority to the US Provisional Patent Application of the same title, which was filed on Sep. 11, 2012, having application No. 61/699,386, which is incorporated herein by reference.

The application as filed contains one or more claims having an effective filing date after Mar. 16, 2013.

BACKGROUND OF INVENTION

The present invention relates to cervical restraint collars, and more particularly, collar padding components, systems and assemblies.

The prior art discloses numerous padding designs for neck braces that are for comfort or decorative, as well as a neck brace cover.

Figure 1A:
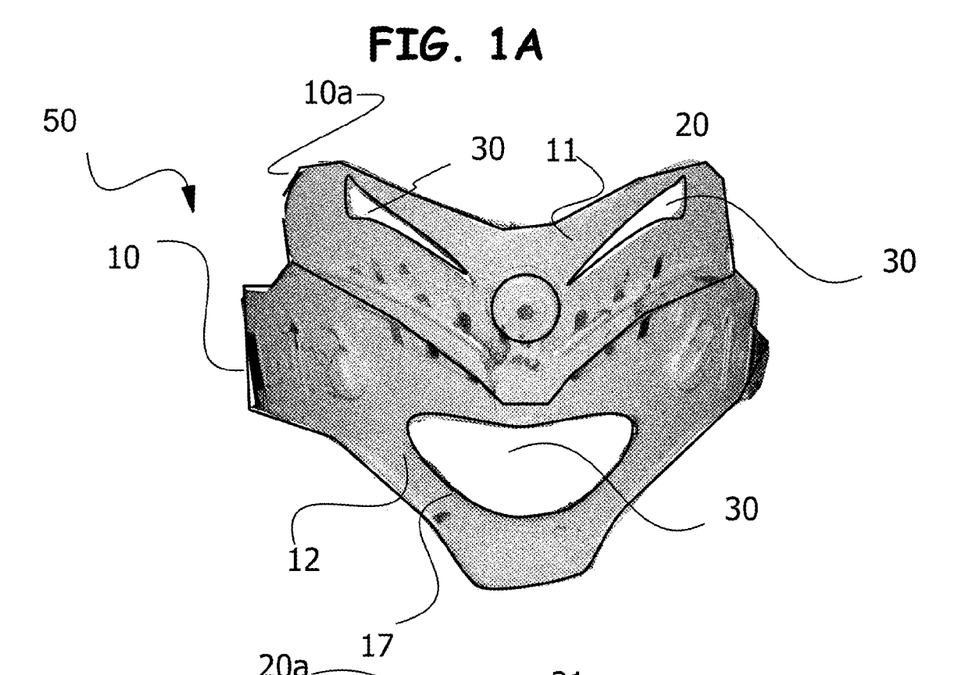
FIGS. 1A and 1B are front elevations of prior art neck brace components.
Figure 1B:
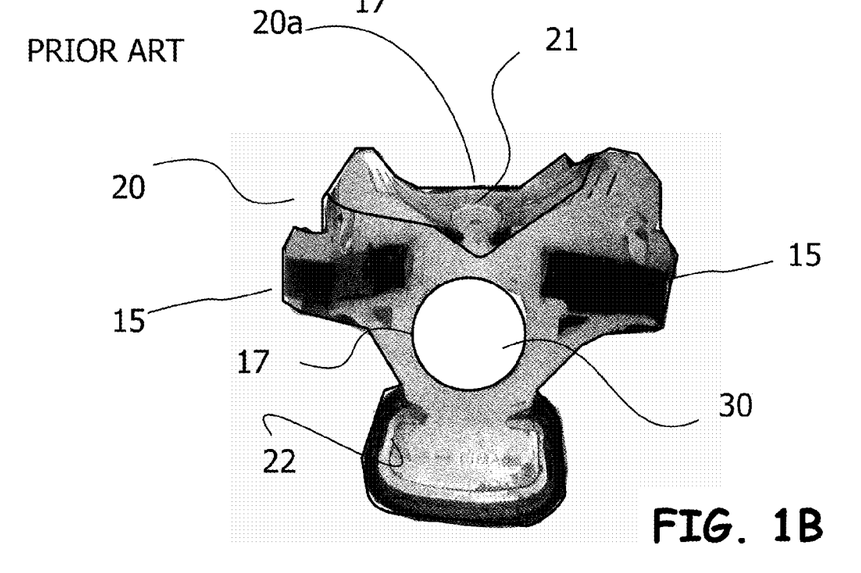
Figure 2:
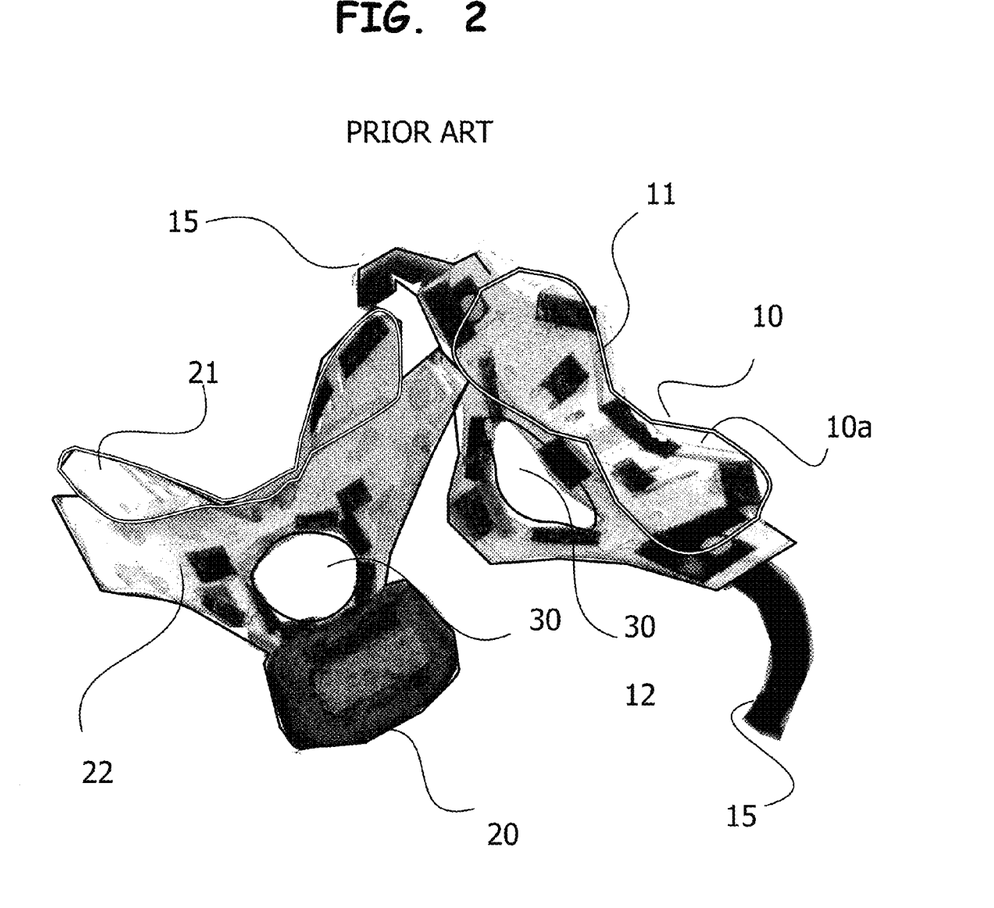
FIG. 2 is a perspective view of the prior art neck brace components of FIGS. 1A and 1B.

As shown in FIG. 1, a representative prior art neck brace 50 has a front member 10 that supports the patients neck at the chin in an upright position by coupling to the chest, whereas the attached rear member 20 support the rear of the neck below and between the ears via a coupling to the patients back.

In some prior art designs, the front member 10 has at least two components, that is an upper components 11 the is placed under the chin, wrapping around both sides of the jaw that can be flexed slightly relative to a connected a Y-shaped lower component 12 having padded plate, that is at the bottom of the Y, which that is biased to lean against the patient's chest about the sternum. Further, the coupling 15 between the upper and lower components is adjustable to accommodate the size and anatomy variations of each patient. The upward extending arms of the Y-shape generally arc around the upper chest just below the connection to the neck. The coupling is typically strapping or belts 15 that attaches to the rear member 20, and extends into slot on the side or edge of the front or other member, 10. When the strap s 15 are or deploy adjacent hook and loop fasteners on their faces they are readily attached to themselves after tensioning, thus securing the front 10 and rear 20 supports together around the patient's upper chest and neck.

The back member 20 may similarly have an upper 21 and lower component 22 that allows some flexure, as well as adjustability. The upper components 12 and 22 are wing shaped with a saddle like central depression for supporting the neck/chin or neck/back of the head junctions. The lower components is generally Y-shaped, with the lower end biased to lean against the back just between the shoulder blades, and the upper arms of the Y-shape arcing around the base of the necks to joint with the opposing arms of the Y-shaped front member. The arms of the front and rear brace members are connected after fitting to the patient via a plurality of straps 15 having an adjustable length to accommodate patient size and anatomy variations. The upper component of the back portion is attached to the lower portion at the crux of the legs of the having a bow tie shape to wrap around the rear of the neck. Upper and lower portions 11/12 or 21/22 connect by adjustable latching slot and pot connected at the sides, with a flexible linked tab connector at the center. The tab flexes so the upper portion conform to the neck shape without stressing the neck and vertebra.

The braces 10 and 20 also deploy internal slots or holes 30 for surgical access, as well as the placement of post surgical drains and the like. The holes or slots not only provide a space open for tubes and drains after surgery but also allow fresh air to flow into the brace and allow the heat from the body around the neck to escape.

The cervical brace systems described above are sold with integrated padding on the inner surfaces, but the outer shell is visible. While the padding will compress to accommodate the patient's external anatomy and is intended to minimize patient discomfort, the softness will diminish from the uncompressed state. More significantly, as the patient can often be wearing these devices for many months, the integrated padding solutions in commercial devices eventually become from uncomfortable and irritate or chafe the skin such that almost any movement become painful.

It is therefore a first object of the present invention to provide greater patient comfort and improved skin care by eliminating the chafing that inevitable occurs with the long term use of such padding.

It is another object of the invention to provide an aesthetic improvement over the appearance of the neck brace.

It is an addition object to obtain improved patient compliance with an improved cervical neck brace or collar.

SUMMARY OF INVENTION

In the present invention, the first object is achieved by providing a kit for a neck brace comprising at least one outer cover for surrounding a relatively rigid portion of the brace member, a first and second pair of inner cushion member, each adopted for interchangeable attachment to an interior portion of the outer cover.

A second aspect of the invention is characterized by a neck brace cover comprising a first brace covering fabric means, an inner cushion means for attachment to the brace covering fabric means, wherein the inner cushioning means is a flexible fabric member partially filled with a conforming material.

Another aspect of the invention is characterized by the neck brace cover in which the conforming material is selected from the group consisting of flowable beads and foam strips.

A further aspect of the invention is characterized by the neck brace cover in which the conforming material is convoluted shape memory foam.

A further aspect of the invention is characterized by the neck brace cover in which the conforming material is convoluted shape member foam having peaks and valleys and flowable beads are disposed within the valleys of the shape memory foam.

Yet another aspect of the invention is characterized by the neck brace cover in which at least one inner cushioning means has 2 or more compartments, one compartment filled with flowable beads and the other compartment filled with foam strips.

The above and other objects, effects, features, and advantages of the present invention will become more apparent from the following description of the embodiments thereof taken in conjunction with the accompanying drawings.

BRIEF DESCRIPTION OF THE DRAWINGS

FIG. 4A is a cross-sectional elevation view of one of the neck brace and attached covers in FIG. 3 illustrating a preferred placement of cushioning members, whereas FIGS. 4B and C are front and rear elevation view of the fabric cover.

FIG. 6A-G are schematic cross-sectional elevation views of alternative embodiments of the cushioning members for attachment to the interior of the fabric covering shown in FIG. 3-5.

DETAILED DESCRIPTION

Referring to FIGS. 1 through 7, wherein like reference numerals refer to like components in the various views, there is illustrated therein a new and improved cervical restraint and padding system generally denominated 100 herein.

Figure 3:
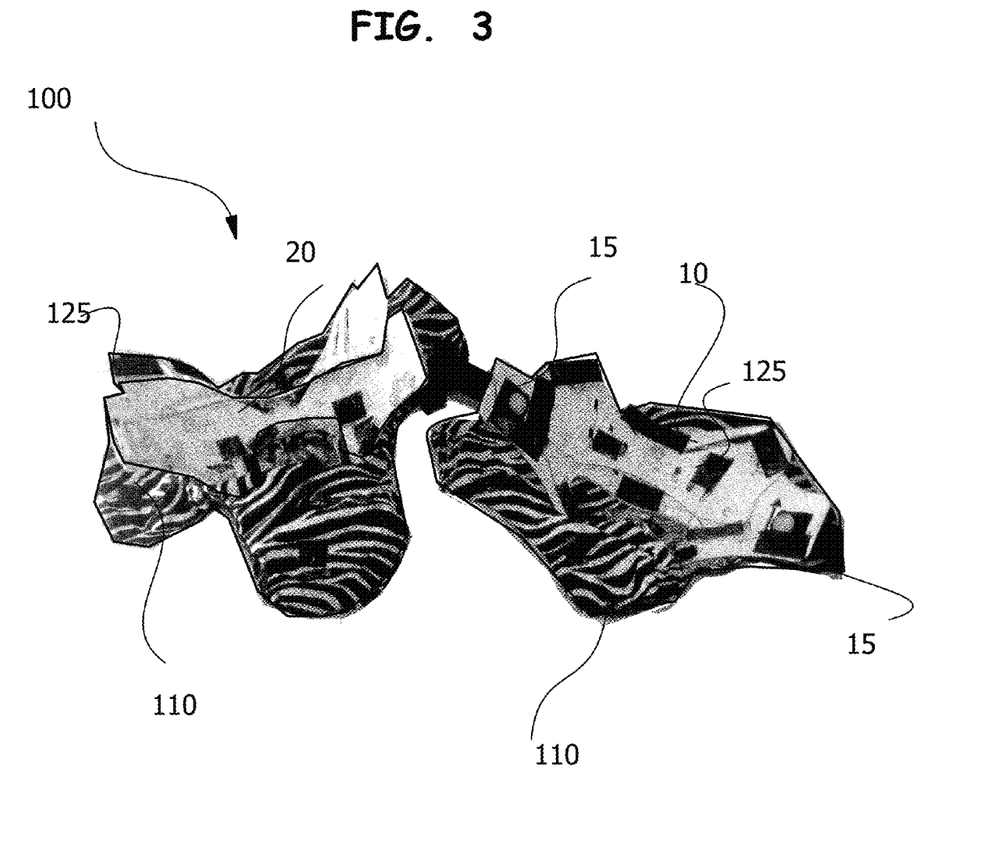
FIG. 3 is a perspective view of the neck brace components of FIG. 1 and FIG. 2AB deploying the inventive cushioning system and covers.

In accordance with the present invention the cervical restraint system 100 deploys a front brace 10 having at least a semi-rigid brace plate for fixing the angulation of the chin with respect to the chest and precluding neck rotation and a rear brace 20 of at least a semi-rigid plate attached at opposing sides to the front brace for limiting a patients neck movement, and at least one fabric cover 110 or slip cover for covering the front or rear brace, but more preferably both the front and rear brace on the inside and outside thereof At least one padding member or pillow 120 has a means 125 for attachment to the interior side of the fabric cover 110, the padding member 120 preferably being a flexible fabric bag 114 partially filled with a conformable supporting material 140, of which various alternative and preferred embodiments are described in further details below with respect to FIG. 6.

In alternative embodiment of the invention the padding member 120/130 deploys as an attachment means 125 hook and loop (Velcro™) fasteners attached to the rear of the fabric cover 100.

Figures 4A, 4B, 4C:
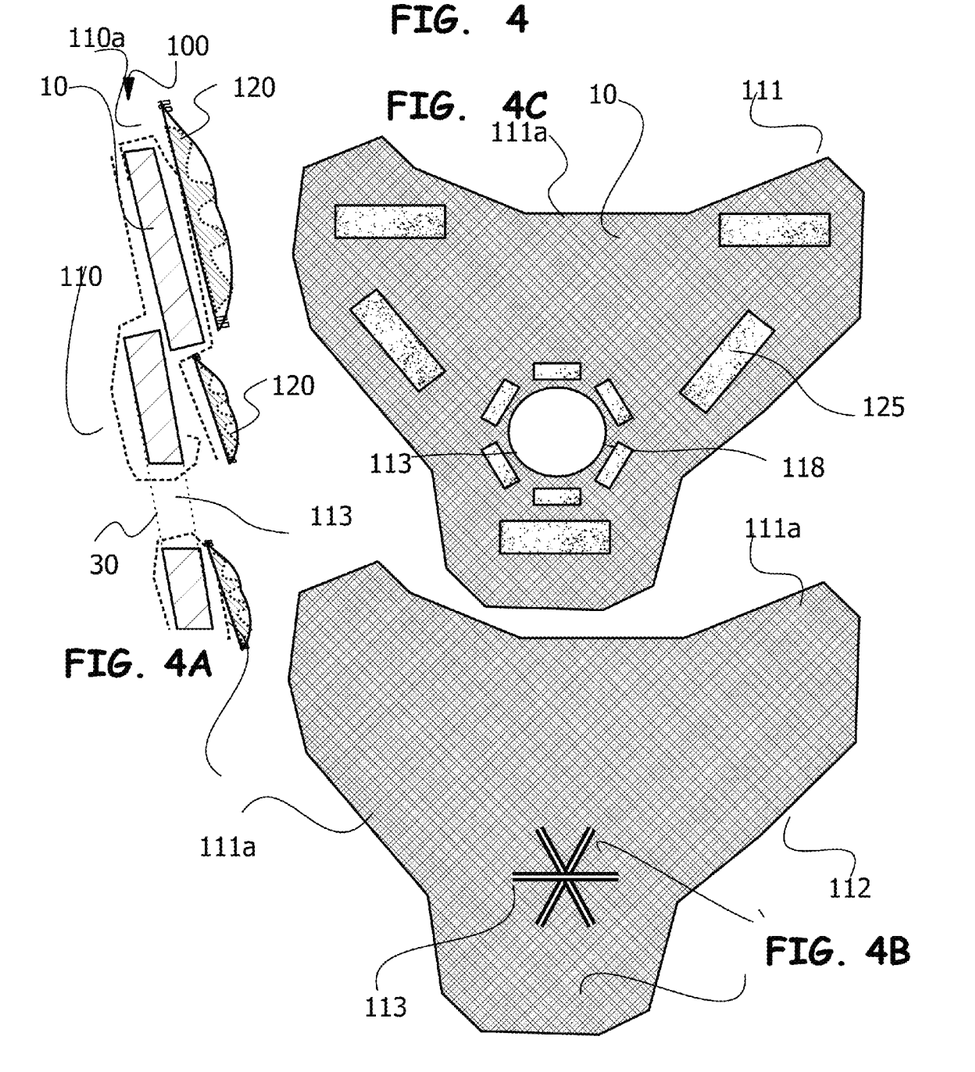
Figure 5:
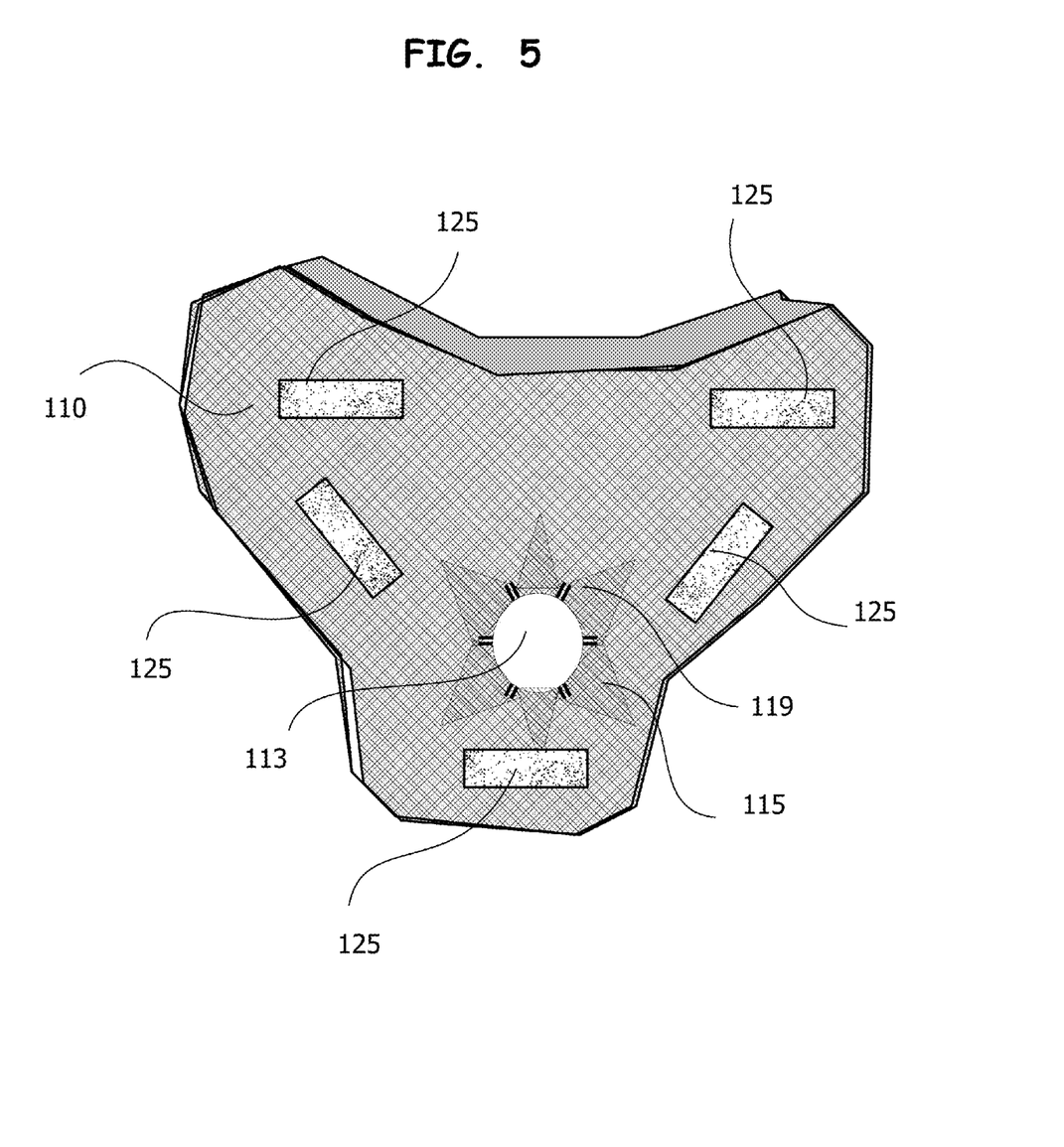
FIG. 5 is a rear elevation view of the fabric cover of FIGS. 4B and 4C after attachment to a neck brace component.

Fabric cover 110 is preferably securely fastening to the front 10 or rear brace 20 by an attachment means 115 that includes extending over the brace and the holes therein to attach to itself. As shown in FIGS. 4B and 4C, such a fabric cover 110 is formed of a front 111 and a rear fabric panel 112 which are sewn together at the common edges 111a, each panel having an aperture 113 or aperture forming portion 113 for inserting a rigid brace member to be covered and/or to coincide with the holes 30 in the braces members. Hence, the brace member 10 or 20 essentially fills the pocket formed between the front and rear fabric member or panel, with such access optionally provided by at least one side slot or opening in which common edges 111a are not sewn together, such that this opening at the adjacent edges penetrates into the interior of the fabric cover 110. More preferably, the fabric cover 110 has an aperture 113 forming portion that folds to connect to itself at aperture 30 in the brace members to provide such an attachment means 115, as shown in FIG. 5. The edges 111a can be completely sewn together provided aperture 113 is large enough for inserting the front or rear brace.

In the embodiment of FIG. 4 such an aperture forming portion 113 comprises a star like slit pattern 117 capable of being opened to form an aperture. At least one of the front 111 and rear panel 112, and optionally both, have this star slit pattern 117 formed at the intended position of aperture 30 in the brace member 10 or 20. Opening the slits to form an aperture in the cover provides triangular portions of the extra fabric 119 between each adjacent slit pairs. Hence, after insertion of a brace member 10 or 20 attachment of this extra fabric 119 from one of the front 111 and rear panel 112 to the other panel securely positions the cover 110 on the brace after insertion, yet avoids closing the brace apertures 30. It also provides a provides a secure attachment of the cover 110 to the brace member 10 or 20 for proper placement of cushions 120 or 130. Thus, the margin 17 of the aperture 30 in the brace 10 or 20 is covered by extra fabric 119 from the aperture 113 that was formed in the front or rear fabric panel. The extra fabric 119 at the aperture 113 in the outer fabric cover panel 111 preferably extends inward to attach to the inner panel 112, and is preferably attached by hook and loop (Velcro™) fasteners 118. As shown in FIG. 4C and FIG. 5, hook and loop (Velcro™) fasteners 125 are also attached to the inner panel face or mated attachment to corresponding hook or loop members 725 attached to the outside of pads 120/130 (FIG. 7) for secure attachment to the portion of the fabric cover 110 that will face the patient when it is inserted on the brace 10 or 20.

Figures 6A, 6B, 6C:
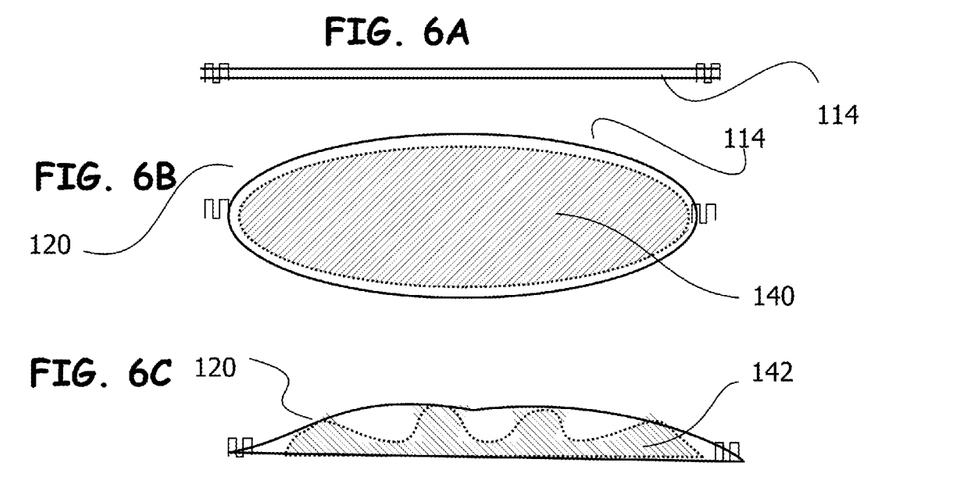

It has been discovered that the most comfortable solution for padding a neck brace is to deploy fabric bags that are only partially filled with a least one of a compressive or flowing medium, which are soft and compliant. By a partially filled fabric bag we mean a compliant fabric bag or pillow 114 that is under filled to the extent that it is not extended to the full external volume permitted by the pliable fabric, or that if it is filled to this shape, it has an unfilled volume. Further, the filling medium 140 should be compliant to reshape the filled volume in response to the user's limited movement. FIG. 6A, shows an unfilled bag formed of 2 fabric panels, whereas FIG. 6B shows the same bag filled.

Padding member 120 or 130 is preferably a flexible fabric member partially filled with a conforming material 140, the flexible fabric being breathable and preferably a cotton fiber fabric or a cotton fiber blend, but is optionally flannel, fleece, microfiber synthetic fabrics. In a preferred embodiments, the padding member 120 is a fabric bag 114 that is filled with flowable beads 141 and another portion 126 filled with foam strips 142. Portion of the padding member with flowable beads 141 is positioned at the brace margins 10a or 20a where the edges thereof are capable of contacting the skin. The shape of the pads are generally, but not exclusively dictated by the shape of the rigid or semi rigid brace itself because the pads must fit in the brace components without sticking too far out under or over the rim of the brace and the pads need to be shaped in such a way that they do not interfere with the air hole. Thus, when the front brace 10 has a Y-shape the attached padding members 120 together generally form a Y-shape.

Figures 6D, 6E:
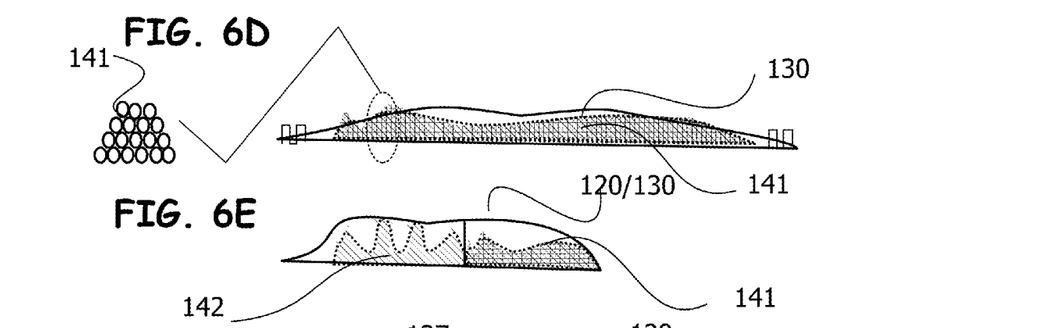

It has been discovered that this requirement can be met by 2 alternative constructions, as well as combination of the same. In a first construction the filler is foam beads 141 that are free flowing within the bag 114. As the fabric bag 114 is under filled, the beads 141 can flow as well as deform when they are disposed between the brace device and the patient's body, as is illustrated in FIG. 6D Alternatively, the requirement for an under filled compliant pillow can be met by under filling the fabric bag with a convoluted shape memory foam 142, as shown in FIG. 6C. Such convoluted foam 142 is typically used in packing crates. As shown in FIG. 6C, the convolutions present peaks that hold up the fabric, possibly to an outer profile that may approach the filled shape. However, as there are air gaps between the peaks, the foam can flow into these gaps, as well as compress in response to the patient's limited movement.

In a more preferred embodiment of the padding members 120/130 illustrated in FIG. 6F, the shape memory foam strips 142 is in a lateral center pockets 127 with soft free flowing bead in a pocket above 128 and a pocket below 129 the lateral center pocket 127. Generally, the shape memory foam 142 is compressed before insertion into the fabric bag 114 that forms the padding member 110 or 120.

Figure 6F:
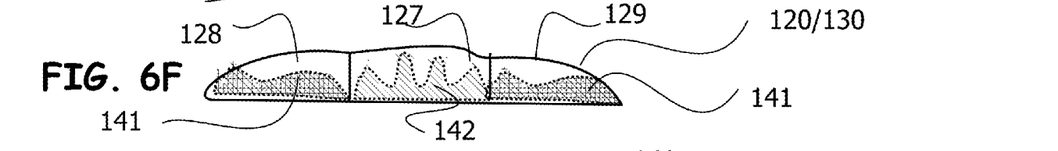
Figure 6G:
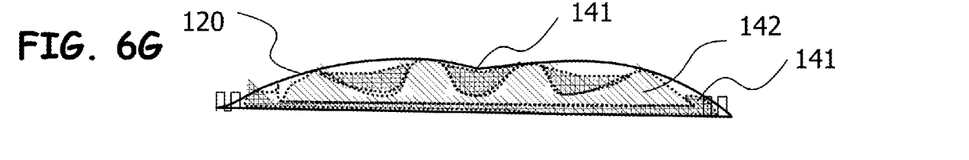

In a more preferred embodiment illustrated in FIG. 6G, the padding members 120 or 130 can be filled in a single pocket with a combination of shape memory foam 142, in the form of strips or the shape of the pocket, along with a plurality of soft free slowing beads 141. The beads are preferably adding both before and after inserting the shape memory foam 142. This configuration gives a foam neck support having intermediate stiffness between the harder fill of only beads (FIG. 6D), and the softer filler of only shape memory foam (FIG. 6C). These various combinations provide users with the opportunity to switch between padding members having three levels of contact force as needed to improve skin comfort. However, this characterization of stiffness is relative to the foam and bead materials actually used for the filler, as the relative firmness of the three types of filling will depend on the stiffness and compressibility of the bead forming material, the relative degree of stuffing of beads in the pocket, and the firmness and compression of the shape memory foam.

It should also be appreciated that another alternative embodiment is the similar combination of the shape memory foam strips 142 with soft free flowing beads 141 in one of the pockets 127 and 128 in the padding members 120/130 illustrated in FIG. 6F.

Hence, the fabric bag 114 when partially filed conforms to shape of at least a portion of the brace members 10 and 20 and when attached to the cover 110 extends over the relatively rigid edges of the brace 10/20 that would otherwise be directly exposed to the patient's skin It should be understood that the padding members are not limited to just the preferred embodiment s described above, as the padding can deploy in whole or part different external and internal materials, such as soft materials and fabrics, such as fleece, microfiber fabrics as an outer cover, as well as the more preferred embodiment of breathable cotton.

It has also been discovered that any type of pad filled with one type of material used the entire time the patient wears the brace will not continue to be as comfortable as it initially was or continue to reduce the pressure points because the weight of the head and the pressure of the rim eventually starts to be felt through any pad. The skin adjusts to the feel and texture of the pad and with pressure from the weight of the head, movement, laying down, riding in a car, or leaning head against the back of the chair these pressure points on the tissue become increasingly aggravated.

Figure 7:
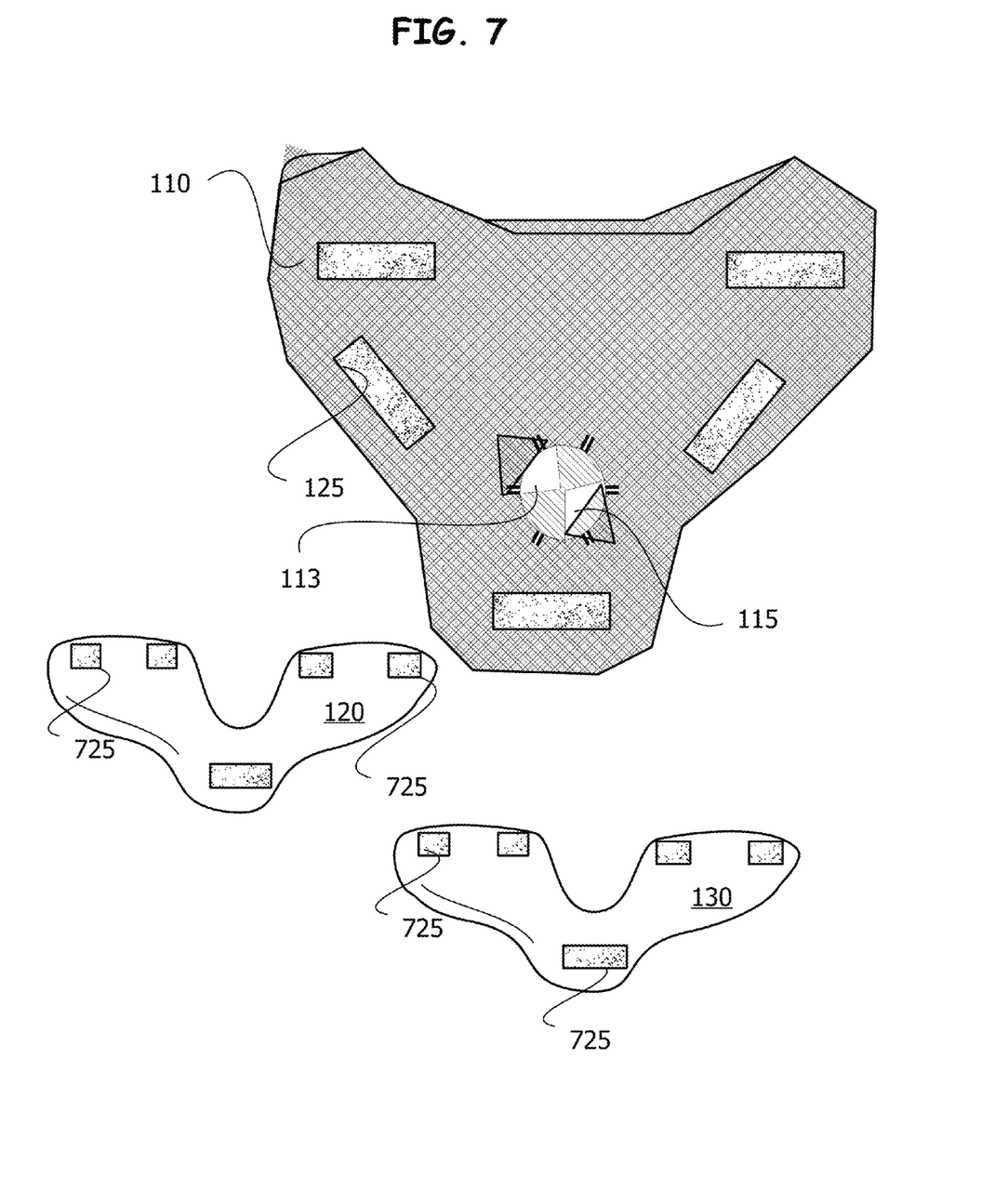
FIG. 7 illustrates in a schematic perspective view a kit comprising a fabric cover and multiple pillows for attachment thereto.

In accordance with another aspect of the invention, a kit 100 as shown in FIG. 7 comprises, at least one but preferably 2 or more fabric covers 110, a first padding member 120 and a second padding member 130, that is exchangeable with the first member for attachment to the fabric cover. Each of the first and second padding members are partially filled with a different conformable supporting material 140. The kit provides for the patient to select from 2 and preferably 3 sets of pads that are interchangeable to be mixed and matched to adjust for comfort and reduce pressure points that may occur over time. More preferably, such a kit 100 includes at least one set of three padding members 120/130 of the same shape with each member of the set having a different level of stiffness to enable the users to vary the contact force exerted by the cushioning member against the skin, when compressed by the brace 10/20, as needed to improve skin comfort.

Hence, the invention described herein in the different embodiments results in greater patient comfort, aesthetic improvement by choosing the outer fabric cover 110 to be decorative and match other clothing, as well as improved skin care and condition due to the non chafing nature of the padding member 120/130, and their ability to deform partially. These improvements in comfort and aesthetics also lead to better patient compliance in using the neck brace.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

I claim:

1. A neck brace cover comprising:
   a) a first brace covering means,
   b) an inner cushioning means for attachment to the brace covering means, wherein the inner cushioning means is a flexible fabric member partially filled with a conforming material, in which at least one inner cushioning means has two or more compartments, in which one compartment is at least partially filled with flowable beads.

2. A neck brace cover according to claim 1 in which a compartment is at least partially filled with a combination of flowable beads and one or more foam strips.

3. A neck brace cover according to claim 2 in which the one or more foam strips is shape memory foam.

4. A neck brace cover according to claim 2 in which the one or more foam strips is convoluted shape memory foam.

5. The neck brace cover brace according to claim 2 in which at least one foam strip is convoluted shape member foam having peaks and valleys and the flowable beads are disposed within the valleys of the shape memory foam.

6. The neck brace cover according to claim 1 in which compartments of flowable beads surround a compartment filled with foam strips.

7. The neck brace cover according to claim 1 the foam strips are a convoluted shape memory foam.

8. A cervical neck brace for a neck having a front and back comprising:
   a) at least one of a second and first relatively rigid portions for surrounding the front and back of the neck respectively, each having a neck facing inner surface and an outward facing surface opposing the inner surface
   b) an outer fabric member disposed to cover the outer surface of at least of the second and first relatively rigid portions with a perimeter portion that extends over edges of the relatively rigid portions to connect with the inner surface thereof for securing the outer fabric member on the at least one of the second and first relatively rigid portions,
   b) at least one inner cushion member adapted for removable attachment from the outer cover disposed on an inner surface of the relatively rigid portion, wherein the inner cushion members is a flexible fabric member at least partially filled with a conforming material selected from the group consisting of flowable beads, foam strips and shape memory foam.

9. The cervical neck brace of claim 8 further in which the at least one inner cushioning member has two or more compartments, in which each compartment is filled to a different extent with the conforming material to provide a difference in a level of stiffness of each compartment.

10. The cervical neck brace of claim 8 wherein each of the two or more compartments is at least partially filled with a conforming material selected from the group consisting of flowable beads, foam strips and shape memory foam.

11. The cervical neck brace of claim 8 wherein the inner cushion members is a flexible fabric member only partially filled with a conforming material selected from the group consisting of flowable beads, foam strips and convoluted shape foam.

12. The cervical neck brace of claim 8 further comprising an outer fabric member disposed to connect with the inner cushion members by extending through a penetration in the at least one of a second and first relatively rigid portions.

13. The cervical neck brace of claim 8 further comprising an outer fabric member disposed to connect with the inner cushion members by extending through a penetration in the at least one of a second and first relatively rigid portions.

14. The cervical neck brace of claim 8 wherein the inner cushion member is adapted for removable attachment by being secured to a perimeter portion of the outer fabric with hook and loop fasteners.

15. A kit for a neck brace comprising:
a) at least one outer cover for surrounding a relatively rigid portion of the neck brace and having an interior portion,
b) at least a first and a second pair of inner cushion members, each adapted for interchangeable attachment to the same interior portion of the outer cover, wherein at least one of the first and second pairs of inner cushion members is a flexible fabric member at least partially filled with a conforming material selected from the group consisting of flowable beads, foam strips and shape memory foam, in which at least one inner cushioning member has two or more compartments, one compartment filled with flowable beads and the other compartment filled with foam strips.

16. The kit for a neck brace according to claim 15 in which compartments of flowable beads surround a compartment filled with foam strips.

17. The kit for a neck brace according to claim 16 in which each of the first, second and third covering members are filled with different conforming material to provide three different levels of stiffness.

18. The kit for a neck brace according to claim 16 in which two or more of the first, second and third covering members are at least partially filled to a different extent with the conforming material to provide two different levels of stiffness.

19. A kit for a neck brace comprising:
a) at least one outer cover for surrounding a relatively rigid portion of the neck brace and having an interior portion,
b) at least a first and a second pair of inner cushion members, each adapted for interchangeable attachment to the same interior portion of the outer cover, wherein at least one of the first and second pairs of inner cushion members is a flexible fabric member at least partially filled with a conforming material selected from the group consisting of flowable beads, foam strips and shape memory foam in which at least one inner cushioning member has one or more compartments, which is filled with flowable beads and at least one foam strip.

20. The kit for a neck brace according to claim 19 in which the at least one foam strip is convoluted shape member foam having peaks and valleys and the flowable beads are disposed within the valleys of the shape memory foam.

21. A kit for a neck brace comprising:
a) at least one outer cover for surrounding a relatively rigid portion of the neck brace,
b) at least a first and a second pair of inner cushion members, each adapted for interchangeable attachment to the same interior portion of the outer cover, wherein at least one of the first and second pairs of inner cushion members is a flexible fabric member at least partially filled with a conforming material selected from the group consisting of flowable beads, foam strips and shape memory foam and further comprising a third inner cushion member adapted for interchangeable attachment to the same interior portion of the outer cover in which each of the first, second and third covering members comprises a different proportion of flowable beads and foam strips to provide three different levels of stiffness.

* * * * *